United States Patent [19]

Robinson

[11] Patent Number: 5,401,625

[45] Date of Patent: Mar. 28, 1995

[54] HISTOLOGICAL COMPOSITION FOR LIGHT MICROSCOPY

[75] Inventor: James V. Robinson, Aurora, Ill.

[73] Assignee: E. K. Industries, Inc., Joliet, Ill.

[21] Appl. No.: 81,644

[22] Filed: Jun. 24, 1993

[51] Int. Cl.⁶ .................. C12Q 1/00; G01N 1/00; C09K 15/00
[52] U.S. Cl. .......................... 435/4; 422/36; 424/3; 436/176; 252/397
[58] Field of Search .......... 252/380, 397, 400.52, 252/408.1; 422/17, 36; 424/3; 435/4; 436/63, 174, 176

[56] References Cited

U.S. PATENT DOCUMENTS

| | | | |
|---|---|---|---|
| 2,554,944 | 5/1951 | Ferrari, Jr. | 8/94.41 |
| 3,546,334 | 12/1970 | Lerner et al. | 424/3 |
| 3,836,433 | 9/1974 | Wirth et al. | 195/68 |
| 3,862,300 | 1/1975 | Wertlake et al. | 424/3 |
| 3,912,450 | 10/1975 | Boucher | 21/54 A |
| 3,961,097 | 6/1976 | Gravelee, Jr. et al. | 427/2 |
| 3,968,248 | 7/1976 | Boucher | 424/333 |
| 3,997,656 | 12/1976 | Wertlake et al. | 424/3 |
| 4,136,161 | 1/1979 | Falkowski et al. | 424/3 |
| 4,169,137 | 9/1979 | Hirschfeld et al. | 424/8 |
| 4,416,998 | 11/1983 | Adams | 436/86 |
| 4,434,234 | 2/1984 | Adams | 436/86 |
| 4,493,821 | 1/1985 | Harrison | 424/3 |
| 4,578,282 | 3/1986 | Harrison | 422/57 |
| 4,588,579 | 5/1986 | Bachhuber et al. | 424/3 |
| 4,666,699 | 5/1987 | Slifkin | 424/7.1 |
| 4,857,300 | 8/1989 | Maksem | 424/3 |
| 4,946,669 | 8/1990 | Siegfried et al. | 424/4 |

OTHER PUBLICATIONS

Carson, Histotechnology A Self—Instructional Text, 1990, ASCP Press, pp. 14–15, 121, 237.
Pearse, Histochemistry Theoretical and Applied, 1968, Churchill Livingstone, pp. 74–76.
Lillie, Histopathologic Technic and Practical Histochemistry, McGraw—Hill, 1976, pp. 29–30, 35–42.
Putt, Manual of Histopathological Staining Methods, 1972, John Wiley & Sons, pp. 20–21.

Primary Examiner—Michael G. Wityshyn
Assistant Examiner—Ralph Gitomer
Attorney, Agent, or Firm—Laff, Whitesel, Conte & Saret

[57] ABSTRACT

A fixative composition for light microscopy including an aqueous solution of glutaraldehyde, trichloroacetic acid, a metallic salt and a surfactant is disclosed.

13 Claims, No Drawings

HISTOLOGICAL COMPOSITION FOR LIGHT MICROSCOPY

FIELD OF THE INVENTION

This invention relates generally to histologic fixatives and, more particularly, to a glutaraldehyde-based fixative composition for light microscopy.

BACKGROUND OF THE INVENTION

Histological fixatives are used in the preparation of tissue specimens for microscopic examination. It is common practice to fix tissue specimens prior to subjecting them to sectioning and then microscopic examination. Chemical fixation techniques are widely utilized because they generally cause minimal damage to the cells of the tissue, are convenient to use, and can be employed with a wide variety of different tissue types.

Formaldehyde has been a widely used fixative. It has been used as the sole or as the principal active agent in fixatives, as well as a component in multi-component fixative compositions. While formaldehyde has many desirable properties in these applications, unfortunately it tends to harden the tissue.

A major concern with the use of formaldehyde is safety. Formaldehyde is considered a carcinogen and histopathology laboratories are subjected to federal regulations regarding its use. The United States Occupational Safety and Health Administration (OSHA) requires the monitoring of employee exposure to formaldehyde. Additionally, the exposure limits, which were originally established in 1987, have been reduced considerably since that time. The time-weighted average, or permissible exposure limit (PEL) for an 8-hour period is 0.75 ppm. An action level of 0.5 ppm and a short-term exposure level of 2.0 ppm have also been established. These restrictions make it increasingly difficult to use formaldehyde as a tissue fixative.

As an alternative, glutaraldehyde, which is not considered a safety hazard, may be used as a histological fixative. Glutaraldehyde has most frequently been used for the fixation of specimens for electron microscopy and preserves ultrastructure better than any of the other aldehydes. However, like formaldehyde, it tends to overharden tissue, so fixation may not be prolonged. Yet, glutaraldehyde penetrates more slowly than formaldehyde. Since it fixes as it penetrates, penetration into the deeper part of the tissue is likely to be impeded, so tissue sections must be thin. Therefore, because of its overhardening and poor penetration properties, glutaraldehyde has not found wide acceptance as a fixative for light microscopy.

Furthermore, glutaraldehyde is not recommended as a fixative if periodic acid-Schiff (PAS) reactions are performed because false-positive results are obtained. Finally, glutaraldehyde irreversibly blocks tissue antigenic determinants.

Therefore, it would be highly desirable to develop a glutaraldehyde-based fixative composition for light microscopy in which the penetration rate is equivalent to or better than that of formaldehyde, so that conventional tissue section thicknesses can be used. It would also be highly desirable to prepare a glutaraldehyde-based fixative composition that will allow PAS reactions to be performed. Furthermore, it would be highly desirable to develop a glutaraldehyde-based fixative composition that does not irreversibly block tissue antigenic determinants. Finally, it would be highly desirable to prepare a glutaraldehyde-based fixative composition that yields tinctorial detail superior to formaldehyde-based fixatives.

SUMMARY OF THE INVENTION

The present invention comprises a fixative composition including glutaraldehyde, trichloroacetic acid, a metallic salt and a surfactant. The resulting non-hazardous glutaraldehyde-based fixative for light microscopy exhibits improved penetration rates and tinctorial detail; it allows PAS reactions to be performed; and, it does not irreversibly block tissue antigenic determinants.

DETAILED DESCRIPTION OF THE INVENTION

The present invention is directed to a fixative composition for light microscopy. The fixative composition comprises an aqueous solution of glutaraldehyde, trichloroacetic acid, a metallic salt and a surfactant.

The glutaraldehyde, on an active basis, should be present in the fixative composition at a level in the range of about 0.75 to about 4% by volume of the overall composition, and preferably at a level of about 1% by volume.

The trichloroacetic acid should be present on an active basis in the range of about 0.5 to about 5% by volume of the overall composition. Preferably, the trichloracetic acid will be at a level of about 1% by volume. In the alternative, glacial acetic acid may be used in accordance with the present invention. If glacial acetic acid is used, it should be present on an active basis in the range of about 2 to 7% by volume of the overall composition, and preferably, at a level of about 1% by volume.

Metallic salts from the group comprising zinc sulfate, copper sulfate, barium sulfate, cadmium sulfate, barium chloride, potassium chloride, mercuric chloride, and lead chloride may be used in accordance with the invention. Zinc sulfate is preferred. The zinc sulfate should be present on an active basis in the range of about 0.75 to about 2.5% by volume of the overall composition, and preferably, at a level of about 1% by volume.

The surfactants which may be used in the fixative composition of the present invention are anionic surfactants. It is preferred that non-foaming surfactants be used. The anionic surfactant should be present in the range of about 0.001 to 0.01% by volume of the overall composition, and preferably, at a level of about 0.0025% by volume.

The tissue to be examined is immersed in the fixative for approximately 4 to 6 hours and then removed and processed by an established histologic tissue processing schedule. Conventional tissue section thicknesses can be used.

The following example is intended to be illustrative of the present invention and to teach one of ordinary skill how to make and use the fixative composition. This example is not intended to limit the invention or its protection in any way.

EXAMPLE

A fixative composition in accordance with the present invention was prepared by mixing together aqueous solutions of the components listed below in the Table.

TABLE

| Component | % by Volume |
|---|---|
| Glutaraldehyde | 1% |
| Trichloroacetic Acid | 1% |
| Zinc Sulfate | 1% |
| Anionic Surfactant | 0.0025% |

Liver tissue was immersed in the fixative composition for approximately 4 to 6 hours, removed, and then subjected to the following processing schedule: 70% ethanol for 2 hours; 80% ethanol for 1 hour; 2 changes of 95% ethanol for 1 hours each; 3 changes of absolute ethanol for 1 hour each; 2 changes of xylene for 1 hour each; and 4 changes of paraffin wax having a melting point of about 56° to 58° C. for ½ hour each. The tissue embedded in the paraffin wax was subsequently sectioned at 3 microns and floated on a water bath. The sections were then put onto glass microscope slides and stained with routine hematoxylin and eosin stain.

The above fixative composition was used to fix liver tissue and demonstrated an excellent penetration rate and tinctorial detail using a light microscope at 10×, 20× and 40×. Also, periodic acid-Schiff (PAS) reaction, which is not generally available when utilizing glutaraldehyde-based fixatives, was achieved. Furthermore, the fixative composition did not irreversibly block tissue antigenic determinants, an undesirable result generally produced by conventional glutaraldehyde fixatives.

While the present invention is described above in connection with preferred or illustrative embodiments, these embodiments are not intended to be exhaustive or limiting of the invention. Rather, the invention is intended to cover all alternatives, modifications, and equivalents included within its spirit and scope, as defined by the appended claims.

What is claimed is:

1. A histological composition for preparing tissue samples for examination by light microscopy consisting essentially of an aqueous solution of glutaraldehyde, trichloroacetic acid, a metallic salt and an anionic surfactant.

2. The fixative composition of claim 1 wherein the amount of glutaraldehyde on an active basis ranges from about 0.75 to about 4% by volume of the overall composition.

3. The fixative composition of claim 2 wherein the amount of glutaraldehyde on an active basis is about 1% by volume of the overall composition.

4. The fixative composition of claim 1 wherein the amount of trichloroacetic acid on an active basis ranges from about 0.5 to about 5% by volume of the overall composition.

5. The fixative composition of claim 4 wherein the amount of trichloroacetic acid on an active basis is about 1% by volume of the overall composition.

6. The fixative composition of claim 1 wherein the metallic salt is selected from the group consisting of zinc sulfate, copper sulfate, barium sulfate, cadmium sulfate, barium chloride, potassium chloride, mercuric chloride and lead chloride.

7. The fixative composition of claim 6 wherein the metallic salt is zinc sulfate.

8. The fixative composition of claim 7 wherein the amount of zinc sulfate on an active basis ranges from about 0.75 to about 2.5% by volume of the overall composition.

9. The fixative composition of claim 8 wherein the amount of zinc sulfate on an active basis is about 1% by volume of the overall composition.

10. The fixative composition of claim 1 wherein the anionic surfactant is non-foaming.

11. The fixative composition of claim 10 wherein the amount of the anionic surfactant ranges from about 0.001 to about 0.01% by volume of the overall composition.

12. The fixative composition of claim 11 wherein the amount of the anionic surfactant is about 0.0025% by volume of the overall composition.

13. A histological composition for preparing tissue samples for examination by light microscopy consisting essentially of: on an active basis, from about 0.75 to 4% by volume glutaraldehyde, from about 0.5 to 5% by volume trichloroacetic acid, from about 0.75 to 2.5% by weight zinc sulfate and from about 0.001 to 0.01% by volume of a non-foaming anionic surfactant.

* * * * *